United States Patent [19]

Rosenberg et al.

[11] Patent Number: 4,921,793

[45] Date of Patent: May 1, 1990

[54] BACTERIAL PROCESS FOR THE PRODUCTION OF DISPERSANTS

[76] Inventors: Eugene Rosenberg, 9 Habrosh Street, Raanana; Eliora Z. Ron, 36 Yehuda Hanassi Street, Tel Aviv, both of Israel

[21] Appl. No.: 927,716

[22] Filed: Nov. 7, 1986

[30] Foreign Application Priority Data

Nov. 7, 1985 [IL] Israel ............................... 76981

[51] Int. Cl.$^5$ ..................... C12P 19/26; C12P 19/04; C12N 1/20; C07G 17/00
[52] U.S. Cl. ......................................... 435/84; 435/99; 435/101; 435/252.1; 536/123; 514/54
[58] Field of Search .................. 435/84, 101, 99, 253; 514/54; 536/123

[56] References Cited

U.S. PATENT DOCUMENTS

| | | | |
|---|---|---|---|
| 4,395,353 | 7/1983 | Gutnick et al. | 435/101 |
| 4,689,322 | 8/1987 | Kulbe et al. | 514/54 |
| 4,703,117 | 10/1987 | Fischer et al. | 536/127 |
| 4,704,360 | 11/1987 | Shoham et al. | 435/101 |
| 4,760,135 | 7/1988 | Diedrich et al. | 536/17.9 |
| 4,762,824 | 8/1988 | Källenius et al. | 514/54 |

Primary Examiner—Johnnie R. Brown
Assistant Examiner—Pamela S. Webber
Attorney, Agent, or Firm—Browdy and Neimark

[57] ABSTRACT

The present invention relates to polymeric dispersing agents for finely divided materials, particularly minerals, which are fermentation products of bacteria. The invention relates to bacterial strains producing such dispersants and to a process for the production of the dispersants by fermentation of such bacteria.

The invention further relates to compositions containing effective quantities of such polymeric fermentation products in order to be effective dispersants for minerals.

12 Claims, 8 Drawing Sheets 4,921,793

BACTERIAL PROCESS FOR THE PRODUCTION OF DISPERSANTS

FIELD OF THE INVENTION

The invention relates to polymeric substances produced by bacteria, which are used as dispersing agents for water-insoluble finely divided solids in an aqueous medium. The novel dispersants can be used for dispersing a variety of minerals. The invention further relates to compositions containing such polymeric dispersants and to processes for producing and for purifying such polymeric dispersants.

BACKGROUND OF THE INVENTION

Microorganisms, which have a large ratio of surface to volume, produce a variety of surface active agents. A wide variety of surface active agents having a molecular weight of less than about 2000 daltons is produced by microbes. Amongst these there may be mentioned substances which are surface active and which are produced by species such as Rhodococcus, Torulopsis, Pseudomonas, Corynebacterium, B. subtilis etc.

A variety of microbial surfactants which are generally mixtures of proteins and polysaccharides are produced by *Acinetobacter calcoaceticus*. Other surfactants are produced by *Candida tropicalis, Pseudomonas aeruginosa,* Phormidium J-1. None of the known surface active substances produced by bacteria, and by the above mentioned microorganisms, are effective as dispersants of finely divided materials.

Dispersing agents are specific surface active substances which are adapted to assist in the formation and in the stabilization of finely divided solids in a liquid, generally in an aqueous system. Dispersing agents are used on a wide scale in various manufacturing processes, such as the production of paper, inks, paints, pharmaceuticals, plastics, dyes, foodstuffs, ceramics, rubber, cement and the like. Dispersants are widely used in mining industries. Such dispersing agents generally exert their activity by adsorption onto the solid particles, resulting in an electric charge of these, which are subsequently surrounded by counterions, resulting in the repulsion of adjacent particles by each other, preventing flocculation and thus maintaining such finely dispersed particles in suspension.

No bacterially produced polymeric dispersing agents for finely divided minerals are known hitherto. The present invention provides novel polymeric substances which are efficient as dispersing agents in comparatively small concentrations. These can be produced in comparatively pure form by fermentation processes.

SUMMARY OF THE INVENTION

The present invention relates to dispersing agents produced by bacteria, which are polymeric substances. They can be used as dispersants in a wide variety of industries set out above. They are effective dispersants for the dispersion into water of substances such as finely divided limestone, calcium carbonate, phosphates (apatites), titanium dioxide, etc.

According to a preferred embodiment of the invention, there are provided polymeric substances useful as dispersing agents for a variety of inorganic material, such as those defined herein, which are produced by certain strains of *Acinetobacter calcoacetious*. These are bacterially produced high molecular weight substances of the polysaccharide type. The substances which have been obtained in an essentially pure homogenous state, are characterized by a high specific activity as dispersants.

The dispersants of the invention are generally heteropolysaccharides containing carboxy groups, and salts of same with cations, as well as amino and/or acylamino-monosaccharide moieties, including acid addition salts of such amino groups. Examples of cations are sodium, potassium or ammonium ions; and the acid addition salts may be with hydrogen chloride or the like.

Such polymeric products produced by bacteria, comprise a mixture of compounds of varying individual molec lar weights.

The invention extends to carboxyl-containing and amino-(or/and acylamino-) containing heteropolysaccharides which are dispersants for minerals which have lower or higher molecular weights than that indicated in the specific examples.

Without this being construed as a restriction on the scope of the invention, however, it is believed that such dispersants will usually possess an average molecular weight either in the range of about 46,000 to about 57,000 as determined by sedimentation velocity analysis, or in the range of about 55,000 to about 68,000 as determined by intrinsic viscosity.

The polymeric product is produced by fermentation of a suitable strain of bacterium *Acinetobacter calcoaceticus,* and in particular by the strains A2 and HE5, which will be described hereinafter. The products of the invention possess also the property of being in certain concentrations a flocculant for minerals in aqueous media, and in particular for limestone, precipitated calcium carbonate, and in particular for limestone, precipitated calcium carbonate, water-insoluble phosphates and titanium dioxide. The products need not be isolated in order to be active as dispersants for minerals. Thus, the invention extends also to a dispersant for inorganic minerals in aqueous media, characterized in that it comprises either the crude broth produced by the bacterial fermentation process, or a partially purified product. The invention moreover, provides aqueous dispersions of minerals, and more particularly of limestone, precipitated calcium carbonate, a water-insoluble phosphate (especially apatite) or titanium dioxide, in which the dispersing agent is a polymeric product described above.

In another aspect, the invention provides a process for preparing the dispersant of the invention, which comprises aerobic cultivation in the presence of nutrients of a bacterium (preferably a strain of *Acinetobacter calcoaceticus* such as A2 or HE5 as described hereinafter) which when grown excretes the desired novel polysaccharides. The crude product may, if desired, be thereafter separated by centrifugation or filtration and, if desired, subjected to further processing comprising (by way of example) precipitation with ammonium sulfate, solvent extraction to remove non-covalent bound lipids, ion-exchange to replace counter ions, dialysis to remove cellular materials, and/or treatment with enzymes to remove proteins.

In a preferred embodiment, the polymeric product is prepared by a process which comprises:
(a) preparing crude material by the process described above, wherein the separation is preferably effected by centrifugation;
(b) subjecting crude material to precipitation with ammonium sulfate and/or solvent extraction and/or ion-exchange and/or dialysis and/or treatment with enzymes;

(c) extracting an aqueous solution of the material obtained in step (b) with phenol at elevated temperature, and preferably separating the phases by decantation followed by centrifugations;

(d) dialyzing the thus-extracted aqueous solution; and (e) removing water from the thus-dialyzed solution, preferably by freeze-drying.

In a particularly preferred embodiment, the further processing step (b) comprises sequential precipitation with ammonium sulfate, separation of the precipitate by centrifugation, dialysis against distilled water and lyophilization.

For preparing aqueous dispersions of minerals, the dispersant may be used as an aqueous solution or slurry or in the form of the dry material.

The invention moreover provides a mixture of the *Acinetobacter calcoaceticus* A2 or HE5 strains in nutrient or spent nutrients for the growth of such bacterium, and at least an appreciable quantity of the hteropolysaccharide excreted by such bacterium.

DETAILED DESCRIPTION OF THE INVENTION

There are provided inter alia processes for the production of biodispersants from, for example, two different strains of *Acinetobacter calcoaceticus*, which biodispersants are excreted into the surrounding medium during the cultivation of these strains in aerated liquid media. The biodispersant may be concentrated and purified from the spent medium by dialysis, ammonium sulfate precipitation and phenol extraction. The most highly purified fraction consists of an anionic heteropolysaccharide (1.4 $\mu$moles carboxyl group per mg. dry weight) with an average molecular weight of approximately 50,000 daltons. This amino-sugar containing heteropolysaccharide, which is a potent dispersant, is referred to herein as Biodispersan.

The novel biodispersants may be used in any partially purified or purified forms. The biodispersants preparations may be solvent extracted to remove non-covalent bound lipids, ion-exchanged to replace counter ions, and treated with enzymes to degrade inactive proteins. The biodispersants may be applied as liquid solutions, slurries, or as a dried powder; they have been shown to be active in dispersing and/or flocculating different forms of calcium carbonate, titanium dioxide and phosphate minerals.

The dispersant properties of the biodispersants indicate that they will also be active on many others minerals.

Isolation and Characterization of *Acinetobacter calcoaceticus* Strains HE5 and A2

Acinetobacter species are widely distributed in nature. The sources of the two Acinetobacters used in the present invention were human hair (strain HE5) and soil (strain A2).

Strains HE5 and A2 of this invention have been classified as *A. calcoaceticus* by the following criteria:

The cells are gram-negative. non-motile, oxidase-negative, aerobic, coccoid rods that grow on McConkey agar, but do not ferment glucose. Additional proof that A2 and HE5 were *A. calcoaceticus* strains was obtained by using the interspecies DNA transformation method of Juni (J. Bacteriol. 112: 917 (1972)). DNA extracted from either HE5 or A2 transformed competent auxotrophic *A. calcoaceticus* BD413.

Additional biochemical and growth characteristics of strains HE5 and A2 are summarized in Tables 3 and 4. Strain A2 is able to grow on and oxidize many more carbon sources than strain HE5.

Strain A2, described above, has been deposited in the German International Culture Collection under Deposit No. DSM 3894. Strain HE5, described above, has been deposited in the German International Culture Collection under Deposit No. DSM 3895.

TABLE 3

| Biochemical Characterization of *A. calcoaceticus* Strains HE5 and A2: | | |
|---|---|---|
| Test* | A-2 | HE5 |
| Glucose fermentation | − | − |
| Glucose oxidation | + | − |
| Hemolysis (5% sheep RBC) | − | − |
| H$_2$S production (Kligler) | − | − |
| Acid + Gas production (Kligler) | − | − |
| Oxidation of galactose | + | − |
| Oxidation of mannose | + | − |
| Oxidation of rhamnose | − | − |
| Oxidation of xylose | + | − |
| Oxidation of lactose | + | − |

*Media for the various tests are described by MacFaddin (Biochemical Tests for Identification of Medical Bacteria. second edition. Williams and Williams. Baltimore. 1980) and in the Manual of Clinical Microbiology. third edition. American Society for Microbiology.

TABLE 4

| Growth of Strains of HE5 and A2 on different carbon sources | | |
|---|---|---|
| Carbon Source* | HE5 | A2 |
| Glucose | − | poor |
| Glucose 0.5% | − | + |
| Sucrose | − | − |
| Sucrose 0.5% | − | poor |
| Arginine | − | + |
| Alanine | + | + |
| Proline | + | + |
| Tryptophane | poor | − |
| Tryptophane 0.01% | + | + |
| Tyrosine | poor | + |
| Ethanol, 2%, 42° C. | + | + |

*Growth was checked at 30° C.; carbon source was added at a final concentration of 0.1% unless otherwise stated. In addition to the carbon source, the media contained 0.11% di-potassium hydrogen phosphate trihydrate. 0.36% potassium dihydrogen phosphate. 0.4% ammonium sulfate. 0.4% magnesium sulfate heptahydrate (final pH 7.0) and 2% agar.

EXAMPLES

EXAMPLE 1

Production of Biodispersants by *A calcoaceticus* Strains HE5 and A2

Analytical Procedures:

Unless otherwise stated, the solid material used for the dispersion assays was powdered limestone from the environs of Jerusalem, crushed and passed through a 325 mesh filter screen. The material contained over 99% calcium carbonate. Precipitated calcium carbonate was a chemically pure product of Merck, Art.2066, batch 5204195. Titanium dioxide was a commercial pigment obtained from a local distributor. The apatite(-phosphate) preparation was prepared from phosphate rock by repeated extraction with citrate buffer. The final, limestone-free, washed preparation was dried and powdered to pass a 325 mesh filter screen.

The standard mineral dispersion assay was carried out as follows:

(1) To a 12 ml conical graduated tube was added 400 mg of one of the powdered minerals (i.e., limestone, apatite or titanium dioxide).

(2) To the powdered mineral was added 3.8 ml of an aqueous solution containing varying concentrations of the biodispersant, and the suspension was mixed by vortexing for 30 sec.

(3) After allowing 30 min for equilibration at room temperature, the suspension was again mixed by vortexing for 30 sec. (time zero) and the tube was allowed to stand undisturbed.

(4) After 30 min, the upper 2 ml was removed carefully and analyzed for remaining dispersed mineral by turbidity in a Klett-Summerson photometer with a green filter (suspensions were diluted into water so that the final reading was less than 150 Klett units (K.U.); data are presented as final K.U. × dilution).

Figure 1:
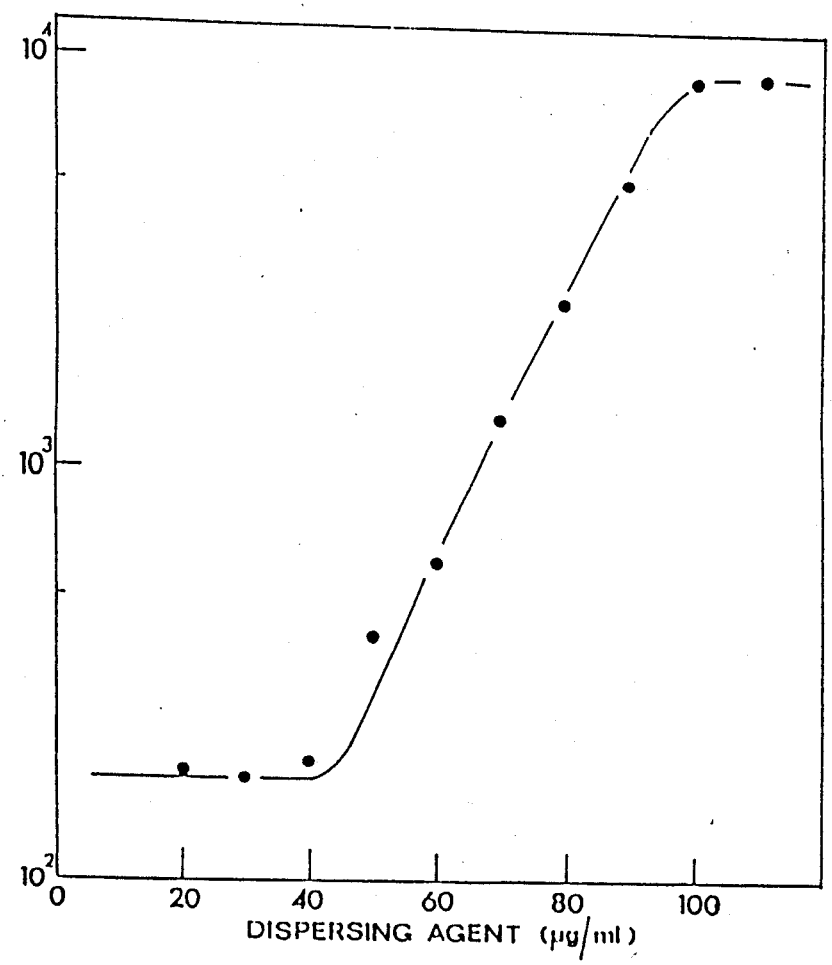
FIG. 1: Standard dispersion assay. The biodispersant agent used in this experiment was the unpurified dialyzed extracellular culture fluid of strain A2.

Using this assay procedure, standard curves of biodispersant activity as a function of concentration were prepared using different preparations of biodispersant. An example is shown in FIG. 1. A unit of dispersing activity is defined as 1000 K.U. using the standard assay procedure. For example, 0.065 mg/ml of the dialyzed A2 biodispersant used in FIG. 1 gave 1 unit of activity. Therefore, the specific activity of that preparation was 1 unit/(0.65) (4 ml), or 3.85 units per mg.

Unless otherwise stated, growth experiments were carried out in 1-liter flasks containing 100 ml of the following medium: 100 mM phosphate buffer, pH 7.0, 0.4% ammonium sulfate, 0.04% magnesium sulfate heptahydrate and 2 ml ethanol. The flasks were incubated with gyratory shaking at 30° C. after inoculation with 1 ml of overnight cultures of either strain A2 or HE5. The cultures were examined after 1, 2 and 3 days for culture turbidity (K.U.) and pH. Samples were then removed, centrifuged to sediment the cells and the extracellular fluid dialyzed extensively against distilled water.

EXAMPLE II

Production of Biodispersants in 4-liter shake flasks and concentration by ammonium sulfate precipitation Twenty 4-liter flasks, each containing one liter of standard medium were inoculated with 7.0 ml of a starter culture of either A2 (10 flasks) or HE5 (10 flasks). The starter cultures were grown for 1 day on the same medium except that they contained 1% ethanol instead of 2% ethanol. The turbidities of the starter cultures at the time of inoculation were 425 and 134 Klett units, respectively, for strains A2 and HE5. The cultures were incubated at 30° C. for 3 days with gyratory shaking (150 rpm). The cells were harvested by centrifugation, washed once and the cell dry weight determined. The supernatant fluids were brought to 55% ammonium sulfate saturation to precipitate the active biodispersant. The precipitates from each of the 10 liters fermentation runs were collected by centrifugation and then dissolved in 450 ml water. After extensive dialyses against distilled water at 4° C., the solutions were lyophilized. The final yields of extracellular materials were 3.7 g of A2 and 2.7 g of HE5.

The specific activities of biodispersants were 6.2 units/mg and 6.3 units/mg for A2 and HE5, respectively. Table 7 summarizes the data on the 10 liter fermentation runs.

TABLE 7

Production of Biodispersants A2 and HE5 in 4-liter flasks

| | Bacterial Cultures | |
|---|---|---|
| Parameters measured | A2 | HE5 |
| Volume | 10 liters | 10 liters |
| Initial turbidity | 3 K.U. | 1-2 K.U. |
| Final turbidity | 470 K.U. | 335 K.U. |
| Final pH | 6.65 | 6.60 |
| Cell yield | 9.2 g | 9.4 g |
| Biodispersant - Dry weight | 3.7 g | 2.7 g |
| Protein | 55% | 85% |
| Dispersing activity | $2.3 \times 10^4$ U | $1.7 \times 10^4$ U |

In the above described examples, biodispersants were obtained by applying gyratory shaking to *A. calcoaceticus* cultures in flasks containing minimal salt medium with two volume percent ethanol. Good yields of biodispersants were obtained from strains HE5 and A2 in this way, but those skilled in the art are aware of numerous other ways in which production could be achieved. For example, conventional submerged fermentations in stirred tanks can be carried out.

EXAMPLE III

Isolation and Characterization of Biodispersant

Deproteinization

The ammonium sulfate precipitated biodispersants described in Example I above, are referred to as crude A2 biodispersant and crude HE 5 biodispersant. These crude materials were further purified by hot phenol according to the method of Zuckerberg et al. (Appl. Environ Microbiol. 37: 414 (1979)).

The combined water extracts obtained from crude biodispersants A2 and HE5 were dialyzed extensively against distilled water and freeze-dried to obtain white fluffy solids, referred to as Biodispersan A2W and Biodispersan HE5W, respectively. The yields of A2W and H 5W were 0.72 g and 0.51 g, respectively. The dispersing specific activities of A2W and H5W were both 15 units per mg, corresponding to a 2.4-fold purification, compared to the crude biodispersants.

Chemical and Physical Properties of Biodispersants A2 and HE5

General Analytical Methods

Protein concentrations were determined by the method of Lowry et al (J. Biol. Chem. 193: 265 (1951)) using bovine serum albumin as standard. Carbohydrate was determined by the phenolsulfuric acid method (Dubois et al., Anal. Chem. 28: 350 (1956)) using glucose as a standard. Reducing sugars were estimated by the arsenomolybdate method (Spiro, Meth. in Enzymol. 8: 7 (1966)) using glucose as a standard. Hexuronic acids were estimated by the carbazole reaction (Dische, Methods of Biochemical Analysis 2:313 (1955)) using glucuronic acid as a standard. Hexosamines were determined by the Indole-HCl method following deamination according to Dische and Borenfreund (J. Biol. Chem. 192:583 (1951)).

Titrations were carried out with a pH meter by a microprocedure in which 0.01 ml portions of 0.1N HCl or NaOH solutions were added with thorough mixing under nitrogen gas (to exclude carbon dioxide) to 3.0 ml solutions to be titrated.

Viscosity was measured on 1.0 ml samples in an Ostwald-Fenske microviscometer at 30° C. A Beckman model E analytical ultracentrifuge equipped with a Schlieren optical system was used for measurement of sedimentation velocity and diffusion constant at 20° C. Absorbance was read on a Gilford model 240 Spectrophotometer. NMR spectra, performed by S. Carmeli, Chemistry Department, Tel Aviv University, were recorded on a Bruker AM-360 Spectrometer with an Aspect 3000 computer and operating at 360.1 MHz and 90.5 MHz for $^1$H and $^{13}$C, respectively. Thin layer chromatography (TLC) was performed on precoated cellulose plates (Merck) using solvent I: ethyl acetate, pyridine, acetic acid, water (5:5:3:1, volume ratios). Sugars and polyols were detected with alkaline silver nitrate (Gal, Anal. Biochem. 24: 452 (1968)). Aminosugars were detected by the ninhydrin spray reagent.

Results:

The $^{13}$C and $^1$H NMR spectra of the purified Biodispersans A2 and HE5 were essentially identical. The two materials also yielded identical titration curves and TLC patterns following acid hydrolysis. Furthermore, Biodispersions A2 and HE5 showed similar dispersing activities towards different minerals (vide infra). The purified Biodispersans A2 and HE5 appeared to be identical, even though they were produced by different Acinetobacter strains. The data presented in this section are for Biodispersan A2, although equivalent data were obtained for HE5.

Purified Biodispersan A2 contained less than 2% protein, gave a negative test for hexuronic acids and a weak reaction with phenolsulfuric acid. Folowing hydrolysis in 3N HCl and 100° C. for 4 hours, the material gave strong tests for reducing sugars and aminosugars. Thus, Biodispersan A2 is an aminosugar-containing biopolymer. The purified bipolymer (1 mg/ml) showed no significant absorption in the range 225–800 nm.

Titration of Biodispersion A2 between pH 2 and 12 showed a single inflection point, corresponding to $pK^1 = 3.2$ (typical of an uronic acid). The material contained 1.4 mole carboxyl groups per mg polymer. Thus, Biodispersan A2 is an anionic biopolymer. The titratable amino groups (pH 7–9) were less than 0.3 μmole per mg, indicating that the aminosugars were mostly N-acylated, as is generally the case with bacterial polysaccharides.

Figure 2:
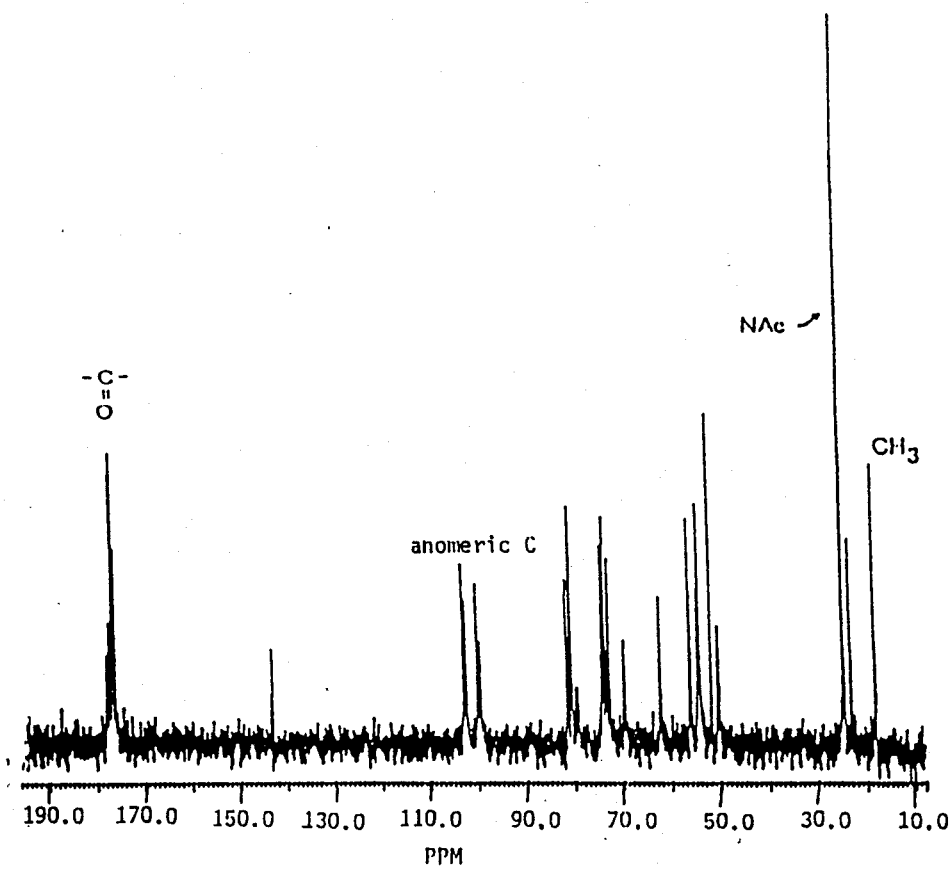
FIG. 2: $^{13}$C-NMR spectrum of Biodispersant A2.
Figure 3:
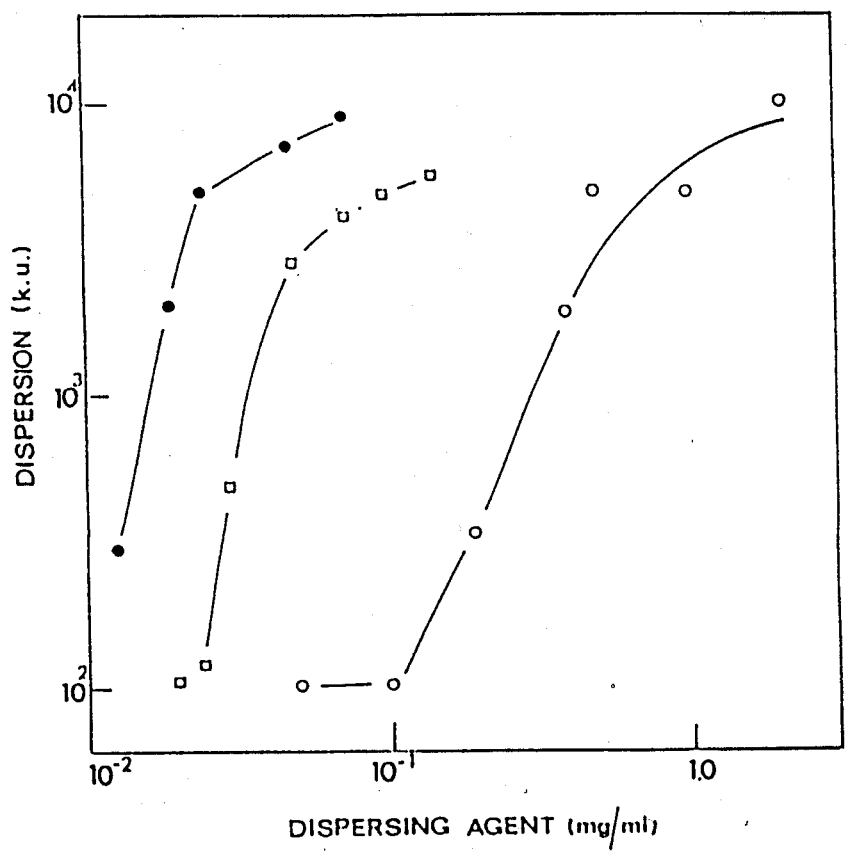
FIG. 3: Dispersion of limestone of biodispersants from HE5: dialyzed cell-free culture broth (O)ammonium sulfate precipitated crude biodispersant (□); purified Biodispersant (●). These symbols are also used in FIGS. 4–8.
Figure 4:
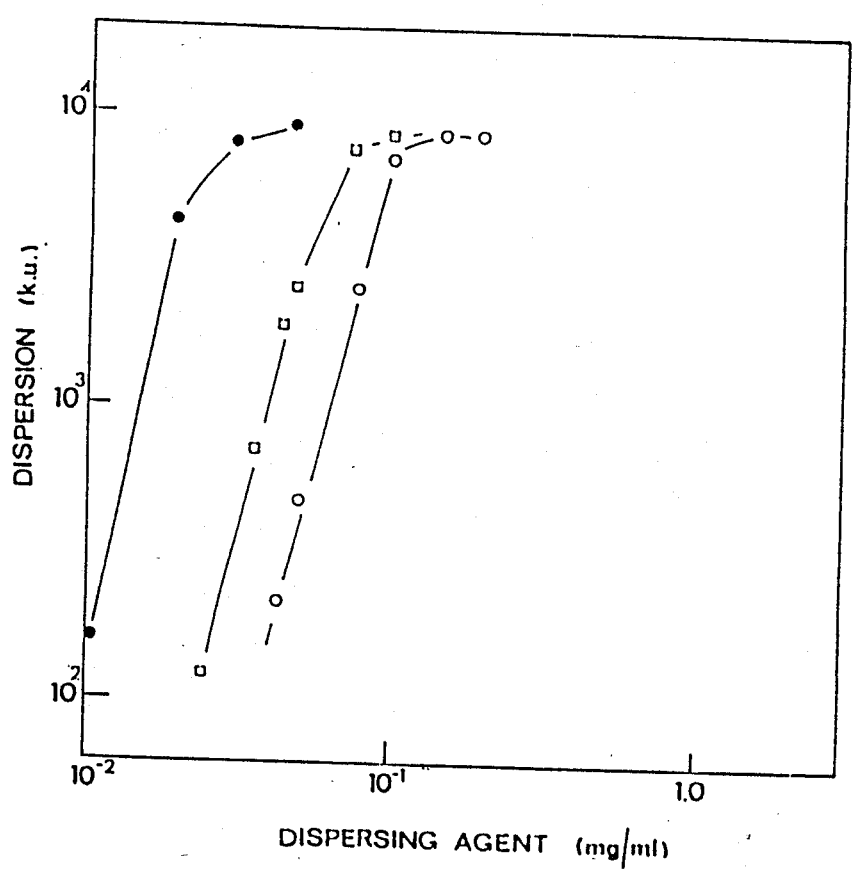
FIG. 4: Dispersion of limestone by biodispersants from A2.
Figure 5:
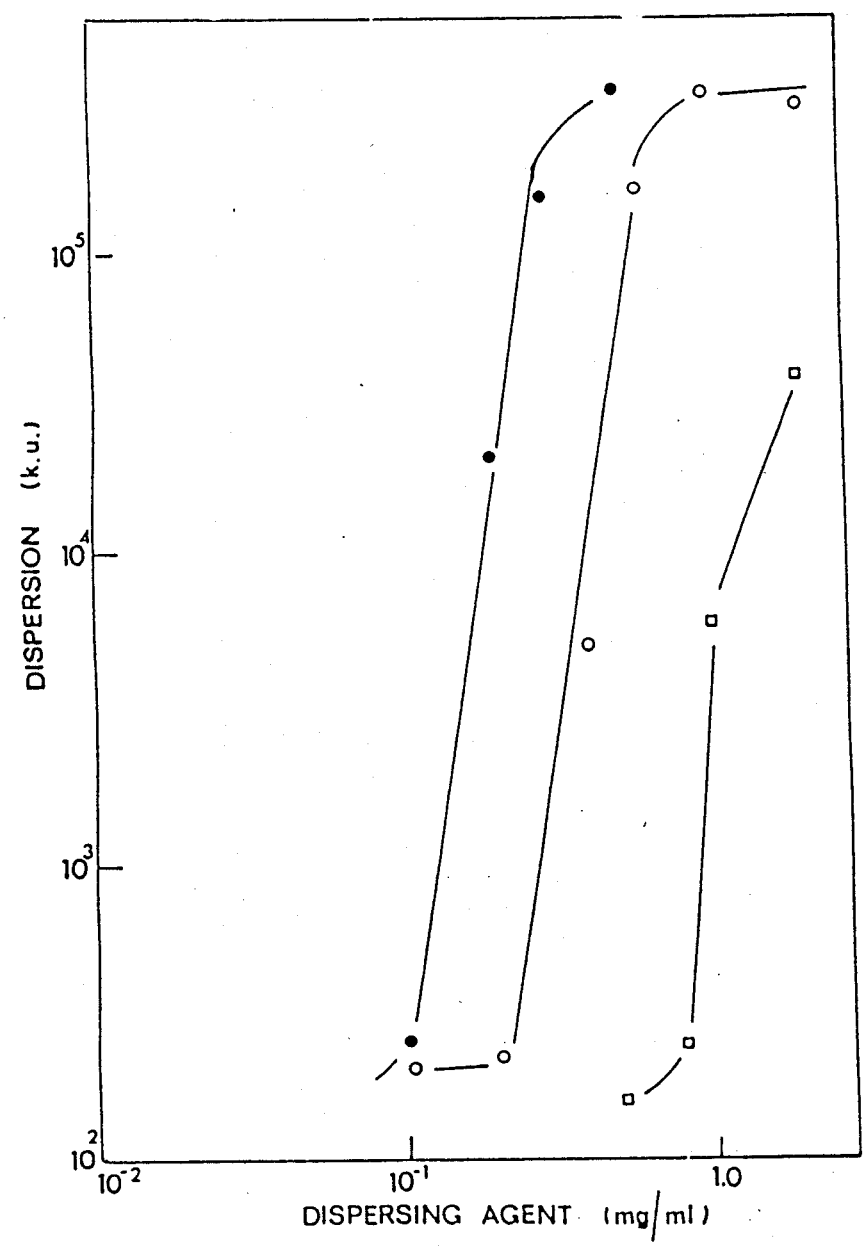
FIG. 5: Dispersion of titanium dioxide by biodispersants from HE5.
Figure 6:
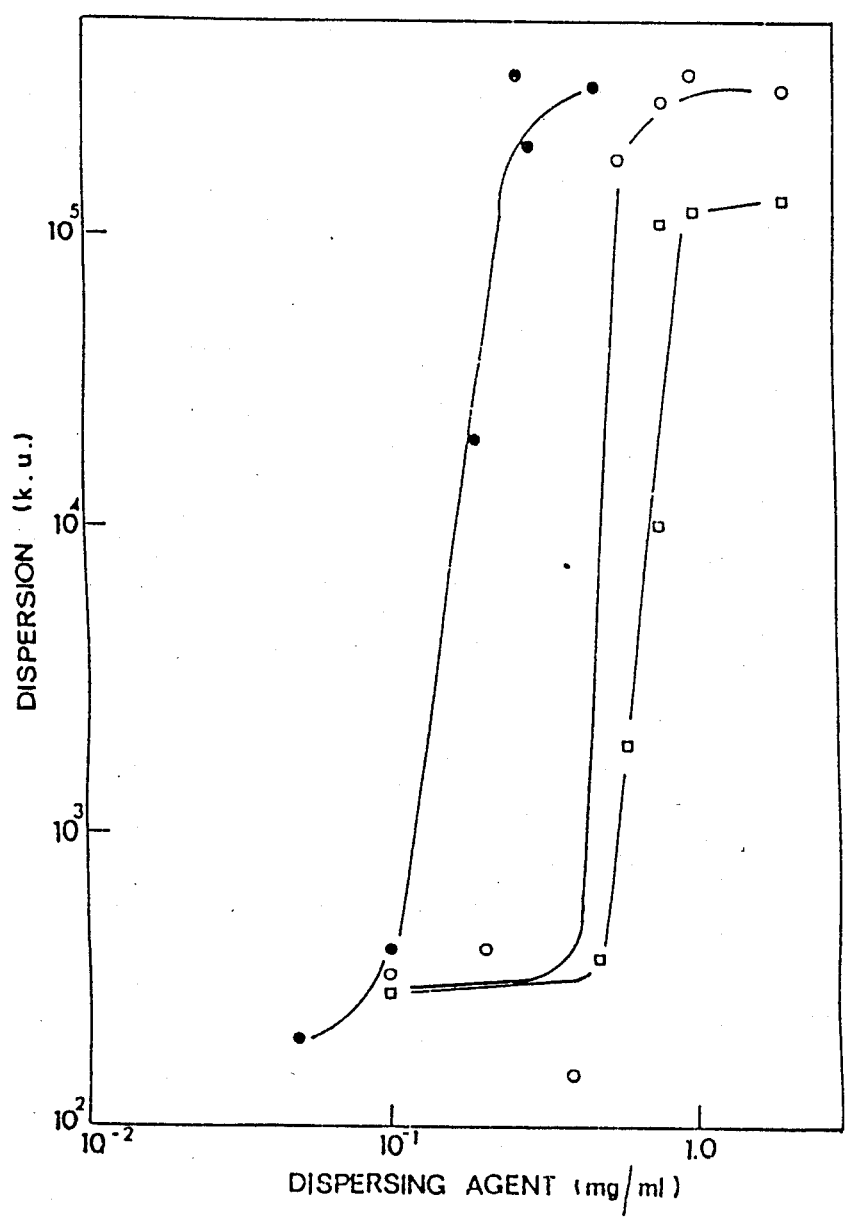
FIG. 6: Dispersion of titanium dioxide by biodispersants from A2.
Figure 7:
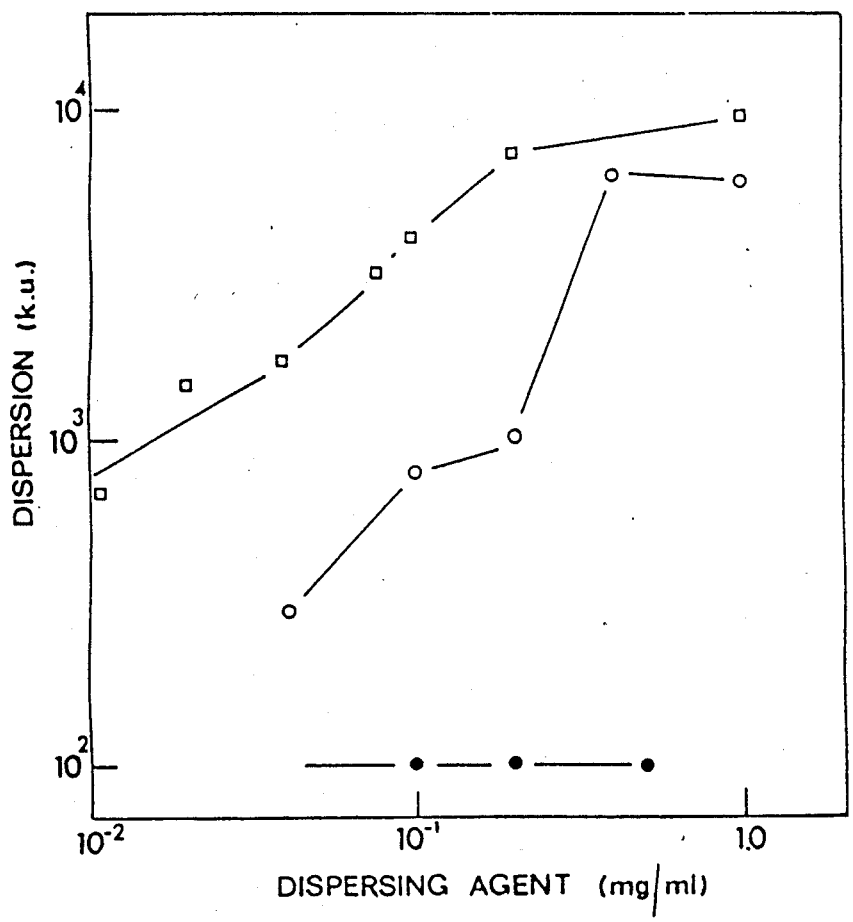
FIG. 7: Dispersion of apatite by biodispersants from HE5.
Figure 8:
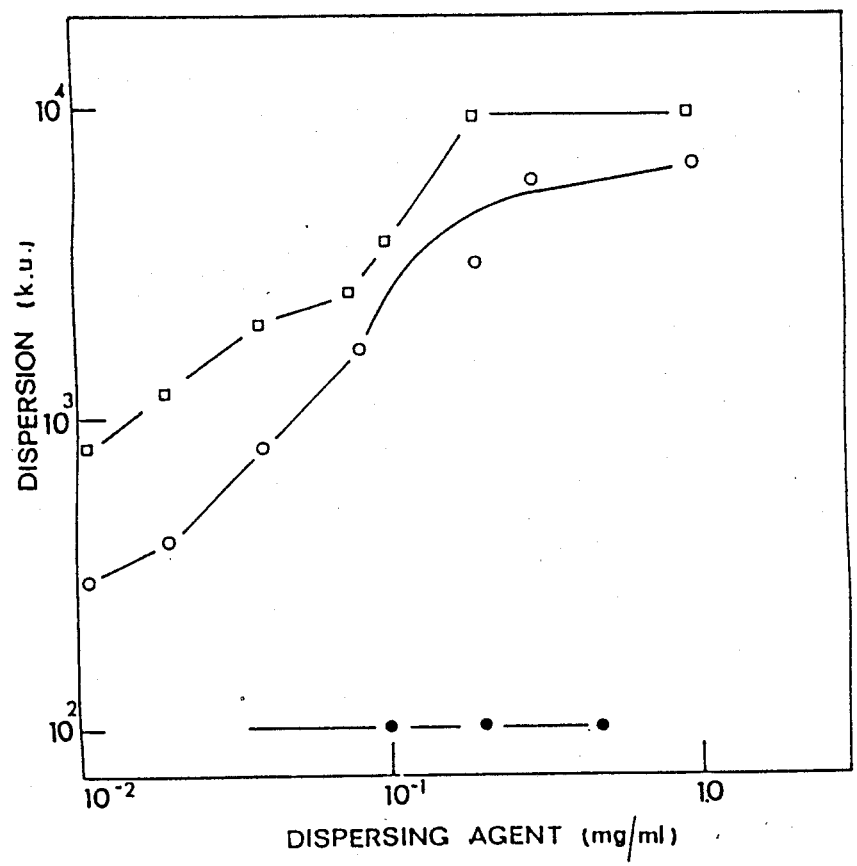
FIG. 8: Dispersion of apatite by biodispersants from A2.

The $^{13}$C-NMR spectrum of Biodispersan A2 showed 27 distinct signals (FIG. 2). The four signals between 99 ppm and 103 ppm occur in the anomeric region of carbohydrates (Gorin, Adv. Carbohydrate Chem. and Biochem. 38: 13 (1981)), suggesting that A2 contains four different monosaccharide units. The five signals between 176 ppm and 178 ppm indicate the presence of carbonyl C atoms. One of these carbonyl groups is likely to be comprised in the carboxyl ion and the remaining four are probably carbonyl moieties of acetyl groups. Accordingly, the multiple signals between 23 ppm and 25 ppm would correspond to the methyl C atoms of the acetyl groups. Since the identical spectrum was obtained after treatment of the polymer with 0.5M NaOH at 100° C. for 15 min, the polysaccharide does not contain O-acetyl groups.

Thus, the acetyl signals arose most likely from N-acetyl groups. The signal at 18 ppm is typical of the methyl group of 6-deoxyhexoses.

The TLC pattern of acid-hydrolyzed Biodispersan A2 (3N HCl, 100° C., 4 hours) developed in solvent I is summarized in Table 8. Three major ninhydrin positive components were observed with mobilities relative to glucosamine of 1.38, 1.03 and 0.69. In addition, there was a streak of ninhydrin-positive and reducing material from the origin to component C. Components A and B are clearly aminosugars, since they gave strong ninhydrin and reducing reactions. Compound C gave a blue ninhydrin reaction and a weak silver nitrate test.

TABLE 8

| | TLC of Hydrolyzed Biodispersan A2[a] | | |
|---|---|---|---|
| | | Reaction | |
| Component | $R^b$ G | AgNO$_3$ | Ninhydrin |
| Standards | | | |
| Glucose | 1.50 | + | — |
| Galactose | 1.33 | + | — |
| Glucosamine | 1.00 | + | Purple |
| Galactosamine | 0.87 | + | — |
| Glucuronic Acid | 0.58 | + | — |
| Galactosamineuronic acid | 0.29 | + (weak) | Tan |
| Hydrolysis products of Biodispersan A2: | | | |
| A | 1.38 | + | Purple |
| B | 1.02 | + | Purple |
| C | 0.69 | + (weak) | Blue |
| Streak | 0–0.5 | + | Brown-purple |

[a]Obtained after 4 hours of hydrolysis in 3 N HCl at 100° C.
[b]Rate of movement of each sugar relative to glucosamine.

Sedimentation velocity analysis of 2 mg/ml Biodispersan A2 showed a single band corresponding to an $S_{20}$ of $1.39 \times 10^{-13}$S or 1.39 Svedberg units. The diffusion coefficient, D, also determined in the analytical centrifuge, was $18.8 \times 10^{-8}$ cm$^2$sec$^{-1}$. Estimating the molecular weight of Biodispersan A2 from the equation:

$$M = RTs\, D^{-1} (1 - V_p)^{-1}$$

where R is the gas constant, T is the absolute temperature, p is the density of the solution and V is the partial specific volume of A2 (assumed to be 0.65 cm$^3$ g$^{-1}$, typical of polysaccharides), yields a weight average molecular weight of 51,400. Alternatively, the molecular weight can be estimated using the determined values for intrinsic viscosity, 440 cm$^3$ g$^{-1}$, and the sedimentation coefficient according to the equation of Scheraga and Mandelkern (J. Am. Chem. Soc. 75: 179 (1953)). The calculated viscosity average molecular weight for Biodispersan A2 was 61,800. Although the chemical structure of Biodispersan A2 has not yet been elucidated, the chemical and physical data presented in this section define the substances as a new anionic, aminosugar-containing heteropolysaccharide.

EXAMPLE IV

Use of biodispersants

The biodispersants of this invention can disperse and-/or stabilize the dispersions of certain mineral powders in water. The effectiveness of a dispersing agent can readily be observed by mixing a 10% slurry of the powder in water and then allowing the suspensions to stand undisturbed. Depending on the size of the particles that constitute the powder and their density, the particles will settle at a fixed rate, leaving a clear upper phase of water. The dispersing agent will slow down the rate of settling. A quantitative measure of the effectiveness of the dispersing agent can be obtained by measuring the rate of sedimentation of the particles (decrease in turbidity of the upper phase) at different concentrations of the dispersing agent. The ability of different preparations of biodispersants from A2 and HE5 to disperse limestone, are shown in FIGS. 3 and 4, to disperse titanium dioxide in FIGS. 5 and 6, and to disperse apatite in FIGS. 7 and 8. The data indicate that the most highly purified preparations, Biodispersans HE5 and A2, disperse limestone at concentrations of less than 0.2 mg/ml, corresponding to a weight ratio of limestone to Biodisperan of greater than 5,000:1. The poorer dispersing power of the crude biodispersants can be attributed to their lower content of active biopolymer. Effective dispersion of the white pigment titanium dioxide required about ten times as much Biodispersan A2 and HE5. Finally, the purified Biodispersans A2 and HE5 were unable to disperse apatite, whereas the crude preparations of biodispersants A2 and HE5 were highly effective in dispersing the artificially prepared (citrate extraction of phosphate rock) apatite preparation.

Low concentrations of biodispersants A2 and HE5 flocculate calcium carbonate (Table 9). The rate of settling of calcium carbonate in water was increased 20% and 75% by 5 μg/ml and 15 μg/ml of crude biodispersant A2, respectively. At 5 μg/ml the weight ratio of bioflocculant to calcium carbonate was 1:20,000. The crude HE5 biodispersant preparation was less potent in flocculating calcium carbonate, requiring 40 μg/ml (1:2,500) to increase the rate of settling by 75%.

TABLE 9

Flocculation of Calcium Carbonate*

| Biodispersant | Settling Rate (clear volume/10 min.) |
|---|---|
| None (control) | 2.0 ml |
| A2 - 5 ug/ml | 2.4 ml |
| 8 ug/ml | 2.8 ml |
| 12 ug/ml | 3.2 ml |
| 15 ug/ml | 3.5 ml |
| HE - 5 ug/ml | 2.2 ml |
| 10 ug/ml | 2.6 ml |
| 20 ug/ml | 2.7 ml |
| 30 ug/ml | 3.0 ml |
| 40 ug/ml | 3.5 ml |

*Ten percent aqueous suspensions of precipitated calcium carbonate containing various concentrations of crude biodispersant were brought to 10 ml in graduate cylinders and allowed to stand undisturbed. After 10 min the volume of the clear upper layer was recorded.

While the invention has been particularly described with respect to certain specific embodiments, it will be appreciated by those skilled in the art that many modifications and variations may be made. Accordingly, the invention is not limited to what has been particularly described, rather it is defined only by the claims which follow.

EXAMPLE V

Biodispersan is also effective in dispersing kaolinite clays. For example, without dispersing agents, 0.8 g Kaolin (BDH, heavy) suspended in 10 ml of water in a graduated tube sedimented at a rate such that, after 30 min, a clear upper layer of 5.6 ml was formed. In the presence of 0.8 mg Biodispersan (ratio of Kaolin to Biodispersan of 1000:1), the Kaolin sedimented much slower. After 30 min, a sediment of only 0.7 ml had formed with a turbid upper phase of 11,000 Klett units. Even after 16 h standing, the upper phase was still turbid (K.U. of 4,600).

EXAMPLE VI

Biodispersan is also effective in suspending certain organic compounds. For example, when 65 mg of large amphorous particles of Oil Red (BDH) were gently mixed with 5 ml water, the Oil Red particles floated to the air/water interface within 5 sec. However, the same experiment performed in the presence of 15 mg Biodispersan, resulted in the Oil Red particles remaining suspended in the water for 20-30 minutes.

We claim:

1. A polymeric substance, useful as dispersing agent for water-insoluble finely divided solids in an aqueous medium, consisting essentially of the purified fermentation product of a bacteria, consisting of a polysaccharide containing carboxy groups, salts thereof, as well as amino- or acylamino monosaccharide moieties, and acid addition salts of these, having an average molecular weight of the polysaccharide molecules of 45,000 to 57,000 determined by sedimentation analysis and about 55,000 to 68,000 determined by measurements of intrinsic viscosity.

2. A polymeric substance useful as a dispersing agent for water-insoluble finely divided solids in an aqueous medium, consisting essentially of the purified fermentation product of *Acinetobacter calcoaceticus* strain A2 or HE5.

3. A polymeric substance useful as dispersing agent for water-insoluble finely divided solids in an aqueous medium, having a spectrum of FIG. 2.

4. A process for the production of a polymeric dispersing agent according to claim 2, which comprises cultivating under aerobic conditions said strain of *Acinetobacter calcoaceticus* until an adequate concentration of the polymeric product is obtained in the culture medium.

5. A process according to claim 4, where the crude is worked up by sedimentation or centrifugation, precipitation with ammonium sulfate, solvent extraction, dialysis to remove cellular material or treatment with an enzyme to remove proteinaceous material.

6. A process according to claim 4 further comprising purifying said polymeric product.

7. A dispersing agent for solid minerals of fine particle size, selected from limestone, calcium carbonate, water-insoluble phosphate, titanium dioxide and clays, which contains an effective quantity of a polymeric substance claimed in claim 2.

8. A biodispersant system according to claim 7, where the concentration of the polymeric substance varies from 1 to 500 to 1 to 5000 by weight calculated on the aqueous medium.

9. A dispersing agent for solid minerals of fine particle size, selected from limestone, calcium carbonate, water-insoluble phosphate, titanium dioxide and clays, which contains an effective quantity of a polymeric substance claimed in claim 1.

10. A biodispersant system comprising a dispersing agent according to claim 9, in an aqueous system where the concentration of the polymeric substance varies from 1 to 500 to 1 to 5000 by weight calculated on the aqueous system.

11. A dispersing agent for solid minerals of fine particle size, selected from limestone, calcium carbonate, water-insoluble phosphate, titanium dioxide and clays, which contains an effective quantity of a polymeric substance claimed in claim 3.

12. A biodispersant system comprising a dispersing agent according to claim 11, in an aqueous system where the concentration of the polymeric substance varies from 1 to 500 to 1 to 5000 by weight calculated on the aqueous system.

* * * * *